United States Patent
Tang et al.

(10) Patent No.: US 9,084,807 B2
(45) Date of Patent: Jul. 21, 2015

(54) COMPOSITION COMPRISING LIGUSTROFLAVONE, RHOIFOLIN AND HYPERIN AND ITS PHARMACEUTICAL APPLICATION

(75) Inventors: Chunshan Tang, Jiangxi (CN); Ning Xie, Jiangxi (CN); Xiaoling Yang, Jiangxi (CN); Wuqing Lv, Jiangxi (CN); Zhiyong Li, Jiangxi (CN); Jingying Ye, Jiangxi (CN); Difa Liu, Jiangxi (CN); Fan Cheng, Jiangxi (CN)

(73) Assignees: JIANXI SHANXIANG PHARMACEUTICAL CO. LTD., Xinshanzhen, Anyuanxian, Ganzhou, Jiangxi (CN); JIANGXI QINGFENG PHARMACEUTICAL RESEARCH CO., LTD., Shahe Industrial Park, Ganzhou, Jiangxi (CN)

( * ) Notice: Subject to any disclaimer, the term of this patent is extended or adjusted under 35 U.S.C. 154(b) by 155 days.

(21) Appl. No.: 13/816,105

(22) PCT Filed: Aug. 4, 2011

(86) PCT No.: PCT/CN2011/078016
§ 371 (c)(1),
(2), (4) Date: Feb. 8, 2013

(87) PCT Pub. No.: WO2012/022223
PCT Pub. Date: Feb. 23, 2012

(65) Prior Publication Data
US 2013/0131000 A1    May 23, 2013

(30) Foreign Application Priority Data

Aug. 16, 2010   (CN) .......................... 2010 1 0253775

(51) Int. Cl.
| A61K 31/7048 | (2006.01) |
| A61K 9/00 | (2006.01) |
| A61K 31/352 | (2006.01) |
| A61K 45/06 | (2006.01) |
| A61K 47/18 | (2006.01) |
| A61K 36/185 | (2006.01) |

(52) U.S. Cl.
CPC ............... *A61K 31/7048* (2013.01); *A61K 9/00* (2013.01); *A61K 9/0095* (2013.01); *A61K 31/352* (2013.01); *A61K 36/185* (2013.01); *A61K 45/06* (2013.01); *A61K 47/18* (2013.01); *A61K 2236/30* (2013.01)

(58) Field of Classification Search
None
See application file for complete search history.

*Primary Examiner* — Layla Bland
(74) *Attorney, Agent, or Firm* — Tianhua Gu; Global IP Services

(57) ABSTRACT

Disclosed is a composition comprising ligustroflavone, rhoifolin and hyperin, which is prepared according to rational weight ratio: 40% to 80% ligustroflavone, 5% to 45% rhoifolin and 1% to 40% hyperin. The composition can be used as a neuraminidase inhibitor for preventing and treating influenza, and can be formulated into pharmaceutically acceptable dosage forms.

7 Claims, No Drawings

COMPOSITION COMPRISING LIGUSTROFLAVONE, RHOIFOLIN AND HYPERIN AND ITS PHARMACEUTICAL APPLICATION

CROSS REFERENCE TO RELATED PATENT APPLICATION

The present application is the U.S. national stage of PCT/CN2011/078016 filed on Aug. 4, 2011, which claims the priority of the Chinese patent application No. 201010253775.1 filed on Aug. 16, 2010, which application is incorporated herein by reference.

FIELD OF THE INVENTION

The present invention relates to a composition comprising ligustroflavone, rhoifolin and hyperin, and its pharmaceutical application.

BACKGROUND ART

Nowadays, the increasingly rampant influenza virus is closely related to respiratory diseases and some systemic diseases thereof. With an enormous population and particular living habits which are liable to transmit the virus, China is one of the countries with a high incidence of influenza. The average annual incidence per capita ranges from 0.3 to 0.7 times, let alone 2-4 times in focus groups.

The influenza severely threatens our human existence. Especially speaking, the new varieties of influenza virus, can not only cause other secondary microbial infections, but also directly lead to organ damages and allergic reactions causing death.

Unfortunately, the current therapies, such as inflammatory reaction treatment according to the corresponding clinical symptoms offer only palliative care. Currently, the most common methods for preventing and treating influenza are vaccinating, taking nonspecific antiviral Chinese traditional medicine and administrating a kind of neuraminidase inhibitor—oseltamivir phosphate (Tamiflu). However, the drawbacks of influenza vaccination lie in its' group selectivity, low protective rate and short protective period for only 3-6 months.

At present, although claimed to have antiviral effect, most nonspecific antiviral Chinese medicines are not against the influenza virus and their antiviral act mechanism still remains unknown.

Our previous studies on the treatments of Pathogenic cold indicate that not all Chinese traditional medicines have a definite effect on inhibiting the influenza virus.

As a neuraminidase inhibitor, "oseltamivir phosphate (Tamiflu, (3R,4R,5S)-4-acetamide-5-amino-3(1-propoxy ethyl ester)-1-cyclohexene-1 carboxylic acid ethyl ester phosphate)" has a specific inhibitory effect on the influenza virus. However, it is expensive and may cause vomiting, nausea, insomnia, headache, abdominal pain, diarrhea, dizziness, fatigue, nasal congestion, sore throat, cough and other side-effects.

Tamiflu's effect on patients with dysfunction liver or intestinal organ will be weakened as the medicine works through esterase conversion to active metabolite, thus playing an inhibition effect of neuraminidase. In addition, the patients with renal insufficiency should take the medicine with caution.

Traditional Chinese medicine believes that the turpinia montana leaf can clear away heat and toxic materials, relieve sore throat and diminish swelling as well as promote blood circulation and stop pain, so it can be used for acute tonsillitis and pharyngitis, sore throat and tumble pain. Ligustroflavone, rhoifolin and hyperin are the main components of the turpinia montana leaf.

With the function of nourishing liver and kidney, improving eyesight and blackening hair, the ligustrum lucidum is mainly used for curing vertigo and tinnitus, soreness of waist and knees, premature whitening of hair, blurred vision and weakness of eyesight. Thus, it is mainly used to treat chronic bronchitis, hepatitis, hyperlipidemia, diabetes, menopause syndrome, infertility and atherosclerosis in recent years. Ligustroflavone is one of the main components of ligustrum lucidum. With the functions of dispelling cold, eliminating dampness, promoting circulation of qi and dissolving phlegm, the pummelo peel is used in the treatment of cold cough, throat itching, excessive phlegm, dyspepsia and vomit. Rhoifolin is one of the essential ingredients of pummelo peel. With the functions of soothing the liver, clearing heat and promoting diuresis as well as relieving swelling and pain, the hypericum perforatum is used for negative emotion, qi stagnation and depression, joint swelling and pain and difficult urination. As one of the key components of hypericum perforatum, the hyperin has shown a good protective effect on myocardial ischemia reperfusion, cerebral ischemia reperfusion and cerebral infarction and has the functions of analgesia, antioxidation, myocardium and liver protection. However, there's no proof that turpinia montana leaf and its contained ligustroflavone, rhoifolin and hyperin, the ligustrum lucidum and its contained ligustroflavone, the pummelo peel and its contained rhoifolin as well as the hypericum perforatum and its contained hyperin possess the functions of inhibiting the infection and reproduction of influenza virus as well as inhibiting the neuraminidase.

SUMMARY OF THE INVENTION

The purpose of the invention is to provide a composition comprising ligustroflavone, rhoifolin and hyperin, which can inhibit the influenza virus neuraminidase from hydrolyzing the sialic acid on the cell surface, preventing the influenza virus from combining with the cell surface receptors and entering into the cells and reducing the generation of the influenza virus within the cells, thus effectively and specifically inhibiting influenza virus replication. More importantly, the composition comprising ligustroflavone, rhoifolin and hyperin provided in the invention can overcome the side reaction of the existing drugs.

In the composition comprising ligustroflavone, rhoifolin and hyperin provided in the invention, the molecular formula of the ligustroflavone is $C_{33}H_{40}O_{18}$, the molecular weight is 724.2 and the structural formula is as follows:

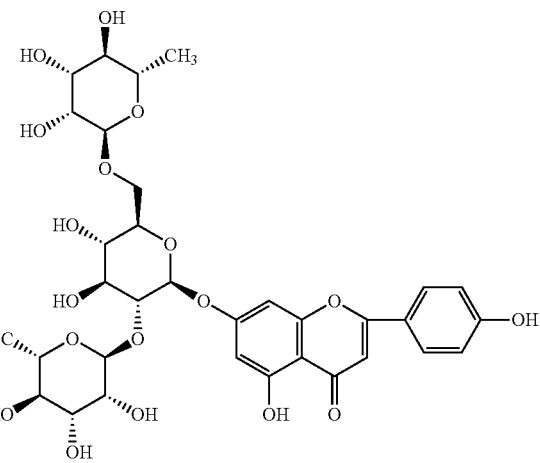

The molecular formula of the rhoifolin is $C_{27}H_{30}O_{14}$, the molecular weight is 578.52 and the structural formula is as follows:

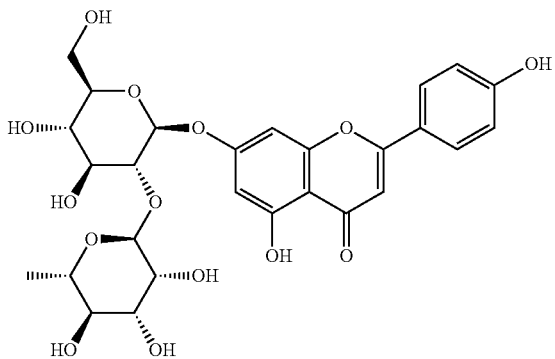 [SMILES: C[C@@H]1O[C@@H](O[C@H]2[C@H](Oc3cc(O)c4c(=O)cc(-c5ccc(O)cc5)oc4c3)O[C@H](CO)[C@@H](O)[C@@H]2O)[C@H](O)[C@H](O)[C@H]1O]

The molecular formula of the hyperin is $C_{21}H_{20}O_{12}$, the molecular weight is 464.38 and the structural formula is as follows:

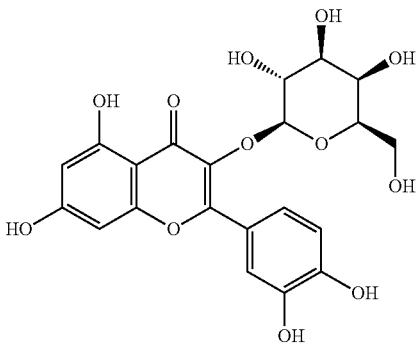 [SMILES: O=c1c(O[C@@H]2O[C@H](CO)[C@H](O)[C@H](O)[C@H]2O)c(-c2ccc(O)c(O)c2)oc2cc(O)cc(O)c12]

The composition comprising ligustroflavone, rhoifolin and hyperin is prepared according to rational weight ratio: 40%-80% ligustroflavone, 5%-45% rhoifolin and 1%-40% hyperin.

Preferred, the composition comprising ligustroflavone, rhoifolin and hyperin is prepared according to rational weight ratio 45% to 75% ligustroflavone, 10% to 40% rhoifolin and 5% to 35% hyperin.

Preferred, the composition comprising ligustroflavone, rhoifolin and hyperin is prepared according to rational weight ratio: 50% to 70% ligustroflavone, 15% to 35% rhoifolin and 10% to 30% hyperin.

Preferred, the composition comprising ligustroflavone, rhoifolin and hyperin is prepared according to rational weight ratio 55% to 65% ligustroflavone, 20% to 30% rhoifolin and 15% to 25% hyperin.

Preferred, the composition comprising ligustroflavone, rhoifolin and hyperin is prepared according to rational weight ratio 58% ligustroflavone, 25% rhoifolin and 17% hyperin.

Furthermore, the invention provides the extraction method of the composition, of which ligustroflavone, rhoifolin and hyperin are extracted from turpinia montana leaf as follows: turpinia montana leaf is reflux extracted by 30%~90% ethanol 5 to 15 times, and each refluxing process lasts 1 to 3 hours for 1 to 3 times and then filtrated. The filtrate is mixed and ethanol is recovered. The aqueous solution is eluted through macroporous resin column. The elution part is collected and decompression dried. This procedure yields the total glycoside of ligustroflavone, rhoifolin and hyperin. After seperating, mix the flow portion respectively, crystallize and get the pure ligustroflavone, rhoifolin and hyperin.

Preferred, the ligustroflavone, rhoifolin and hyperin are obtained according to the following extraction method: take the turpinia montana leaf, add 70% ethanol which is 12 times amount of the leaf Conduct reflux extraction for 1.5 hours and filtrate, then dissolve the filter residue 70% ethanol which is 10 times amount of the leaf, conduct reflux extraction for 1.5 hours and filtrate, mix the extracting solution for two times, recover the ethanol, elute the water solution through macroporous resin column, collect and decompression dry the elution part.

Preferred, the aqueous solution is eluted through D101 macroporous resin column by water, 5%~10% ethanol, 30%~55% ethanol and 1% sodium hydroxide solution in sequence, collect and decompression dry the 30%~55% ethanol elution part.

Preferred, the mixed total glycosides are subjected to silica gel column and Sephadex LH-20 column chromatography seperation. Mix the flow portion of ligustroflavone, rhoifolin and hyperin respectively, crystallize and get the pure components.

The invention also provides the application of preventing and treating influenza and its complication by the drug contains ligustroflavone, rhoifolin and hyperin.

Preferred, the composition comprising ligustroflavone, rhoifolin and hyperin is used to inhibit the influenza virus.

Preferred, the composition comprising ligustroflavone, rhoifolin and hyperin is used to inhibit the influenza virus FM1.

Preferred, the composition comprising ligustroflavone, rhoifolin and hyperin is used to inhibit the neuraminidase.

Preferred, the complication refers to kidney failure.

Preferred, the complication refers to spleen injury or/and lung injury.

The ligustroflavone, rhoifolin and hyperin described in the invention can be the crude samples or monomeric compounds extracted from a variety of herbs such as turpinia montana leaf, ligustrum lucidum, pummelo peel and hypericum perforatum.

Finally, the invention also provides a pharmaceutical preparation of in which the active ingredient is the composition comprising ligustroflavone, rhoifolin and hyperin.

The experimental data proves that the composition comprising ligustroflavone, rhoifolin and hyperin in the invention can effectively inhibit the neuraminidase. The capability of inhibiting neuraminidase varies according to the dosage of the composition and appears the positive correlation.

The composition comprising ligustroflavone, rhoifolin and hyperin can inhibit the influenza virus from entering the cells and inhibit the influenza virus that has entered the cells from replicating and proliferating by inhibiting the neuraminidase on the influenza virus surface, so as to reduce the infection and growth of the influenza virus against the cells, prevent and treat the influenza and its complications and also inhibit the influenza virus neuraminidase from hydrolyzing the sialic acid on the cell surface, causing that the influenza virus cannot be combined with the cell surface receptors and enter into the cells and reducing the generation of the influenza virus within the cells. More importantly, the composition comprising ligustroflavone, rhoifolin and hyperin provided in the invention can avoid the side reaction of the existing drugs.

Without medical and pharmaceutical experiments of inhibiting the influenza virus infection and replication or inhibiting the neuraminidase, researchers can not predict the good effect of the composition comprising ligustroflavone, rhoifolin and hyperin for preventing and curing cold caused by influenza.

In summary, the invention provides the composition comprising ligustroflavone, rhoifolin and hyperin,Which can afford significant technological effect.

DETAILED DESCRIPTION OF PREFERRED EMBODIMENTS

Embodiment 1

In the composition comprising ligustroflavone, rhoifolin and hyperin provided in the invention, the molecular formula of the ligustroflavone is $C_{33}H_{40}O_{18}$, the molecular weight is 724.2 and the structural formula is as follows:

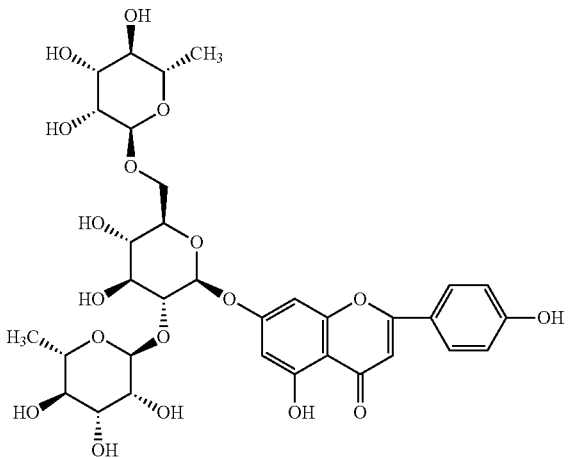 [SMILES: C[C@@H]1O[C@@H](OC[C@H]2O[C@@H](Oc3cc(O)c4c(=O)cc(-c5ccc(O)cc5)oc4c3)[C@H](O[C@@H]3O[C@@H](C)[C@H](O)[C@@H](O)[C@H]3O)[C@@H](O)[C@@H]2O)[C@H](O)[C@H](O)[C@H]1O]

The molecular formula of the rhoifolin is $C_{27}H_{30}O_{14}$, the molecular weight is 578.52 and the structural formula is as follows:

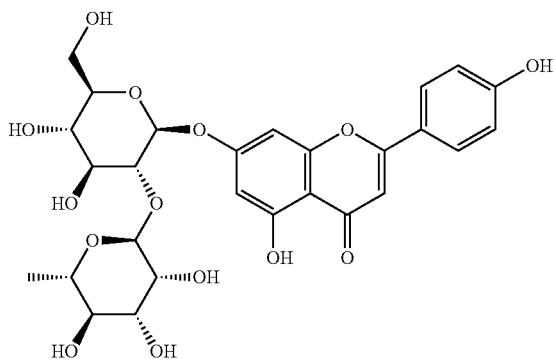 [SMILES: C[C@@H]1O[C@@H](O[C@H]2[C@H](Oc3cc(O)c4c(=O)cc(-c5ccc(O)cc5)oc4c3)O[C@H](CO)[C@@H](O)[C@@H]2O)[C@H](O)[C@H](O)[C@H]1O]

The molecular formula of the hyperin is $C_{21}H_{20}O_{12}$, the molecular weight is 464.38 and the structural formula is as follows:

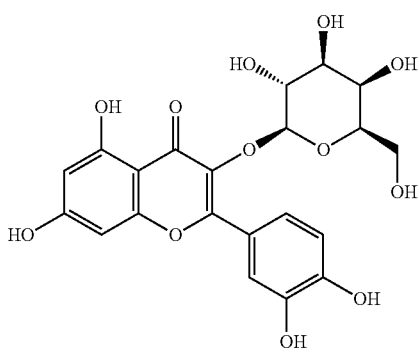 [SMILES: O=c1c(O[C@@H]2O[C@H](CO)[C@H](O)[C@H](O)[C@H]2O)c(-c2ccc(O)c(O)c2)oc2cc(O)cc(O)c12]

Take 1000 g turpinia montana leaf, add 70% ethanol which is 12 times amount of the leaf, then dissolve the filter residue in 70% ethanol which is 10 times amount of the leaf, conduct reflux extraction for 1.5 hours and filtrate, mix the extracting solution of the two times, recover the ethanol, elute the aquaous solution through the treated D101 macroporous resin column. Elute the water solution with water, 10% ethanol, 45% ethanol and 1% sodium hydroxide solution in sequence, collect the 45% ethanol elution part, decompression dry, get the mixed total glycosides of 30% or above ligustroflavone, rhoifolin and hyperin, which are subject to silica gel column and Sephadex LH-20 column isolation. Mix the flow portion of ligustroflavone, rhoifolin and hyperin respectively, crystallize and get the pure ligustroflavone (3.5 g, purity: 98.5%), rhoifolin (1.5 g, purity: 98.7%) and hyperin (1 g, purity: 98.2%). Through comparing UV, IR, ESI-MS, 1H-NMR and 13C-NMR characteristics by the standard substance's, the structures of the above three compounds are confirmed.

In addition, the ligustroflavone, rhoifolin and hyperin provided in the invention can also be extracted respectively, as shown in the following embodiment.

Embodiment 2

Take 1000 g ligustrum lucidum, add 65% ethanol which is 10 times amount of the ligustrum lucidum, conduct reflux extraction for 2 hours and filtrate, then add 8 times the amount of 65% ethanol in the filter residue, conduct reflux extraction for 1.5 hours and filtrate, mix the extracting solution and recover the ethanol. Subject the aquaous solution through the treated D101 macroporous resin column. Elute the aquaous with water, 8% ethanol, 40% ethanol and 1% sodium hydroxide solution in sequence. Collect and decompression dry the 40% ethanol elution part, get the mixed total glycosides of above 30% ligustroflavone. Subject the total glycoside to silica gel column and Sephadex LH-20 column for seperation. Mix the flow portion of ligustroflavone, crystallize and get the pure ligustroflavone (19.2 g, purity: 98.6%). Through comparing UV, IR, ESI-MS, 1H-NMR and 13C-NMR characteristics by the standard substance's, structure of ligustroflavone are confirmed.

Embodiment 3

Take 1000 g pummelo peel, add 10 times the amount of 65% ethanol, conduct reflux extraction for 2 hours and filtrate, then add 8 times the amount of 65% ethanol in the filter residue, conduct reflux extraction for 1.5 hours and filtrate, mix the extracting solution, and recover the ethanol. Subject the aquaous solution through the treated D101 macroporous resin column. Elute the aquaous solution with water, 10% ethanol, 45% ethanol and 1% sodium hydroxide solution in sequence, collect and decompression dry the 45% ethanol elution part, and get the mixed total glycosides of above 30% rhoifolin. Subject to silica gel column and Sephadex LH-20 column isolation. Mix the flow portion of rhoifolin, crystallize and get the pure rhoifolin (4.6 g, purity: 98.5%). Through comparing it's UV, IR, ESI-MS, 1H-NMR and 13C-NMR characteristics with the standard sample's, hence identified the structure of rhoifolin.

Embodiment 4

Take 1000 g hypericum perforatum, add 12 times the amount of 70% ethanol, conduct reflux extraction for 1.5 hours and filtrate, then dissolve the filter residue with 10 times the amount of 70% ethanol, conduct reflux extraction for 1.5 hours and filtrate, mix the extracting solution, recover the ethanol, subject the aquaous solution through the treated D101 macroporous resin column. Elute the aquaous solution with water, 10% ethanol, 45% ethanol and 1% sodium hydroxide solution in sequence. Collect and decompression dry the 45% ethanol elution part, get the mixed total glycosides of above 30% hyperin. Subject the total glycosides to silica gel column and Sephadex LH-20 column isolation. Mix the flow portion of hyperin, crystallize and get the pure hyperin (8.5 g, purity: 98.6%). Compare it's UV, IR, ESI-MS, 1H-NMR and 13C-NMR characteristics with the standard sample's, hence rhoifolin and determine identified the structure of rhoifolin.

Embodiment 5

Mix, stir and grind the ligustroflavone (14 g), rhoifolin (6 g) and hyperin (3.6 g) uniformly with the proportion of 7:3:1.8 and get the composition (23.6 g) comprising ligustroflavone, rhoifolin and hyperin.

Embodiment 6

Mix, stir and grind the ligustroflavone (12 g), rhoifolin (8 g) and hyperin (4 g) uniformly with the proportion of 3:2:1 and get the composition (24 g) comprising ligustroflavone, rhoifolin and hyperin.

Embodiment 7

Mix, stir and grind the ligustroflavone (10 g), rhoifolin (10 g) and hyperin (6 g) uniformly with the proportion of 5:5:3 and get the composition (26 g) comprising ligustroflavone, rhoifolin and hyperin.

Embodiment 8

Mix, stir and grind the ligustroflavone (8 g), rhoifolin (12 g) and hyperin (8 g) uniformly with the proportion of 2:3:2 and get the composition (28 g) comprising ligustroflavone, rhoifolin and hyperin.

Embodiment 9

Mix, stir and grind the ligustroflavone (6 g), rhoifolin (14 g) and hyperin (10 g) uniformly with the proportion of 3:7:5 and get the composition (30 g) comprising ligustroflavone, rhoifolin and hyperin.

Some preferred embodiments of the weight percentage of the ligustroflavone, rhoifolin and hyperin are provided below in Table 1, but the content of the three components in the present invention is not limited to the values listed in the table.

Nevertheless, the percentage of three components can be reasonable varied by professional staff rather than confined the data in the table.

TABLE 1

Weight Percentages of Ligustroflavone, Rhoifolin and Hyperin in Composition (%)

| Weight percentage of ligustroflavon- | Weight percentage of rhoifolin | Weight percentage of hyperin |
| --- | --- | --- |
| 80 | 15 | 5 |
| 75 | 10 | 15 |
| 70 | 20 | 10 |
| 65 | 34 | 1 |
| 58 | 25 | 17 |
| 55 | 5 | 40 |
| 50 | 35 | 15 |
| 45 | 45 | 10 |
| 40 | 40 | 20 |

Experimental Data 1: Inhibitory Action of the Composition Comprising Ligustroflavone, Rhoifolin and Hyperin on Neuraminidase Activity Take the composition comprising ligustroflavone, rhoifolin and hyperin obtained according to the preparation method in embodiment 5, add an appropriate amount of water to dissolve it, use the neuraminidase inhibitor identification kit to determine the neuraminidase inhibition (N1) potency of the composition, as shown in Table 2.

(1) Standard curve preparation: a. add 70 μl neuraminidase detection buffer solution in each hole of 96-hole luciferase plate; b. add 0, 1, 2, 5, 7.5 and 10 μl H5N1 neuraminidase respectively in each hole; c. add 0~20 μl Milli-Q water in each hole.

(2) Sample preparation: a. add 70 μl neuraminidase detection buffer solution in each hole of 96-hole luciferase plate; b. add 10 μl H5N1 neuraminidase in each hole; c. add 0~10 μl sample of the composition comprising ligustroflavone, rhoifolin and hyperin in each hole; d. add 0~10 μl Milli-Q water in each hole.

(3) Detection steps:
a. Shake and mix for about 1 min;
b. Incubate for 2 min at 37° C., in order to that the inhibitor and H5N1 neuraminidase are fully interacted, meanwhile, incubate the samples for standard curve;
c. Add 10 μl neuraminidase fluorogenic substrate in each hole;
d. Shake and mix for about 1 min;
e. Conduct fluorimetric determination after incubate for 20~30 min at 37. The excitation wavelength is 360 nm and the emission wavelength is 440 nm.

(4) Calculate the inhibition percentage to H5N1 neuraminidase according to the standard curve as well as IC 50 of the composition after building the concentration curve. The neuraminidase inhibition ratio IC 50 of the composition is 0.13 g/L, as shown in Table 2.

TABLE 2

Inhibition Activity of Neuraminidase of the Composition

| Compound | Detection target enzyme | Target enzyme substrate | Compound concentration | Enzyme inhibition ratio (potency) |
| --- | --- | --- | --- | --- |
| Composition comprising ligustro-flavone, rhoifolin and hyperin | Neuraminidase (N1) | Neuraminidase fluorogenic substrate | 1.3 g/L<br>0.13 g/L<br>0.013 g/L | 80.9%<br>50.0%<br>32.4% |

It's clearly shown that:

(1) The component effectively inhibiting neuraminidase can be extracted from the composition comprising ligustroflavone, rhoifolin and hyperin;

(2) With the changes in dosage, the neuraminidase activity inhhicapability of the composition comprising ligustroflavone, rhoifolin and hyperin to inhibit the neuraminidase activity, i.e. the neuraminidase inhibition ratio is also changed correspondingly and appears positive correlation;

(3) By inhibiting the neuraminidase on the influenza virus surface, The composition comprising ligustroflavone, rhoifolin and hyperin can inhibit the influenza virus from entering the cells and inhibit the influenza virus which has entered the cells from replicating and proliferating so as to reduce the infection and growth of the influenza virus against the cells, prevent and treat the influenza and its complications.

Without conducting an experiment of inhibiting the influenza virus infection, replication and inhibition of neuraminidase, medical and pharmaceutical researchers can not know that the composition comprising ligustroflavone, rhoifolin and hyperin has a good effect in preventing and treating influenza.

Experimental Data 2: Inhibitory Action of the Composition Comprising Ligustroflavone, Rhoifolin and Hyperin on Influenza Virus Infected Chick Embryo Take the composition comprising ligustroflavone, rhoifolin and hyperin obtained according to the preparation method in embodiment 5 and use the influenza virus FM1 H1N1 to identify the ability of the composition comprising ligustroflavone, rhoifolin and hyperin to inhibit the replication and inhibition of FM1 influenza virus in the chick embryo. (1) Inoculate FM1 influenza virus solution in allantoic cavity of 10 d chick embryo without specific pathogens for 0.2 ml per embryo, and incubate at 37° C. for 72 h, then observe and calculate the median chick embryo infective dose (EID50).

(2) For determinating the toxic action of the composition on chick embryo, dilute the composition of a series concentration with sterile saline solution, inoculate it in allantoic cavity of 10d chick embryo without specific pathogens for 0.2 ml per embryo and 6 embryos for each concentration, incubate at 37° C., observe the growth and development of the chick embryo. The maximum concentration with which the chick embryo can survive for 96 h is as the drug TD. (3) For determinating the inhibitory action of the composition on the influenza virus in the chick embryo, mix 0.1 ml influenza virus solution and different dilutions of the composition comprising ligustroflavone, rhoifolin and hyperin at 37° C. for 2 h, inoculate it in allantoic cavity of 10 d chick embryo without specific pathogens for 6 embryos in each group and incubate for 72 h at 37° C. The virus attack amount is 50EID50. Meanwhile, set up the virus control and sterile saline solution for normal control and calculate the median infective dose (EID50) of the composition for virus inhibitory action.

(1) The virulence of FM1 influenza virus to the chick embryo is calculated by Reed-Muench method with the EID50 of $10^{-5.07}$. (2) The growth and development of the composition comprising ligustroflavone, rhoifolin and hyperin is basically the same with the normal control group after inoculated in the chick embryo. The chick embryos survive in 96 h. With the stock solution of the composition comprising ligustroflavone, rhoifolin and hyperin added, no chick embryos die, so it can be considered that TD0 is 2.0 g/L. (3) The inhibitory action of the composition comprising ligustroflavone, rhoifolin and hyperin on the influenza virus in the chick embryo is shown in Table 3.

TABLE 3

Inhibitory Action of the Composition Comprising Ligustroflavone, Rhoifolin and Hyperin on Influenza Virus Infected Chick Embryo

| Compound | Drug concentration | With virus infection/case | Without virus infection/case | Infection rate (%) |
|---|---|---|---|---|
| Composition | 1.0 | 0 | 8 | 0.0* |
| comprising | 0.5 | 0 | 8 | 0.0* |
| ligustroflavone, | 0.25 | 0 | 8 | 0.0* |
| rhoifolin and | 0.125 | 5 | 3 | 62.5* |
| hyperin | 0.0625 | 8 | 0 | 100.0 |
| Virus control group | 0.0 | 8 | 0 | 100.0 |
| Normal control group | 0.0 | 0 | 8 | 0.0 |

Compared with the virus control group: *P < 0.05

It can be seen from Table 3 that the composition comprising ligustroflavone, rhoifolin and hyperin with the concentration of 0.125~1.0 g/L has a significant inhibitory action on the influenza virus (P<0.05), $ED_{50}$ is 0.16 ±0.007 g/L and TI is 43.75±3.28.

Experimental Data 3: Impact of the Composition Comprising Ligustroflavone, Rhoifolin and Hyperin on FM1 Influenza Virus Take the composition comprising ligustroflavone, rhoifolin and hyperin obtained according to the preparation method in embodiment 5 and use the influenza virus FM1 H1N1 to identify its' ability of inhibiting FM1 influenza virus. (1) For the measurement of the FM1 virulence to MDCK cells, use the mircomethod of median infective dose of cells (TCID50).

(2) For the measurement of the virulence of the composition to MDCK cells, conduct serial dilution for the composition with serum-free DMEM, inoculate it in singler-layer MDCK cell holes with 100 μl per hole, repeat 4 holes for each dilution grade and set up normal cell control. Culture the plate in 37° C. and 5% $CO_2$ incubator, observe the cytopathic effect (CPE) for 3 consecutive days, record the results with "+~++++" and calculate the median toxicosis concentration (TD50) and maximum non-toxic concentration (TD0) of the drug with Reed-Muench method. (3) Measurement of inhibitory action of the composition comprising ligustroflavone, rhoifolin and hyperin on FM1 influenza virus: place the $5×10^5$/ml MDCK cells in 96-hole plate with 100 μl in each hole, Culture the plate in 37° C. and 5% $CO_2$ incubator, getter the culture solution in the holes in the next day, add 100TCID50 influenza virus solution with 100 μl in each hole, get rid of the supernatant after adsorption at 37° C. for 1 h, wash 2 times with phosphate buffer solution (PBS), take the drug TD0 as the first hole, conduct serial dilution for the composition comprising ligustroflavone, rhoifolin and hyperin with serum-free DMEM and add it in the above cells infected with virus respectively, set up the virus control group and normal control group, place the solution in the 37° C. and 5% $CO_2$ incubator for culture, observe the pathological characteristics of MDCK cells produced by the influenza virus, namely, degeneration and rounding of monolayer cells for 3 consecutive days and calculate the 50% cytopathic effect inhibition concentration (IC50) and therapeutic index (TI) of the drug. TI calculation: TI=TD50/IC50, the larger TI value, the larger safety range is of the drug. Compare the differences of the CPE between the test group and the virus control group with Kruskal-Walis and Mann-Whitney test methods, conduct correlation analysis of the drug dose and the inhibition ratio of the virus-infected cells for avoid cytopathic effect (CPE) and determine whether there is dose-effect relationship.

(1) The virulence of FM1 influenza virus to the chick embryo is calculated by Reed-Muench method with the EID50 of $10^{-4.81}$. (2) TD0 of MDCK cells of the composition comprising ligustroflavone, rhoifolin and hyperin is 0.89 g±0.037 g/L. (3) Conduct inhibition test for 100TCID50 influenza virus by serial dilution of the composition and calculate the median effective dose IC50 and TI values of the drug. The results are shown in Table 4.

TABLE 4

IC50 (g/L) and TI (x ± s) of the Composition Comprising Ligustroflavone, Rhoifolin and Hyperin to FM1 Influenza Virus

| Compound | Target virus | Virus target cell | Influenza virus IC50 (g/L) | Influenza virus TI |
|---|---|---|---|---|
| Composition comprising ligustroflavone, rhoifolin and hyperin | FM1 | MDCK | 0.31 ± 0.009 | 23.36 ± 3.42 |

It can be seen from Table 4 that IC50 of the composition comprising ligustroflavone, rhoifolin and hyperin is low and TI is high. The inhibitory action of the composition on cytopathic effect of FM1 influenza virus is enhanced with the increase of drug dose. The correlation analysis for the inhibition ratio of the drug dose and drug to CPE shows that there is a significant positive correlation between the dose of the composition and the inhibition ratio of the drug to CPE.

Experimental Data 4: Impact of the Composition Comprising Ligustroflavone, Rhoifolin and Hyperin on Mice Spleen Index and Lung Index which Infected Influenza Virus FM1.

Take the composition comprising ligustroflavone, rhoifolin and hyperin obtained according to the preparation method in embodiment 5 and use the influenza virus FM1 H1N1 to identify the death protective action of the composition on the infected influenza virus FM1 in mice. (1) After 10 times of dilution, FM1 influenza virus is inoculated in BALB/C mice with 10 of each group, half male and half female. After be mild anesthetized by diethyl ether, each group is intranasally inoculated different virus dilutions for 20 μl each mouse. Observe the death of mice for 10 d and calculate LD50 equal to $10^{-1.36}$ according to Reed-Muench method. Therefore, to confirm the modeling concentration used in the experiment is 10LD50. (2) Death protective action of the composition comprising ligustroflavone, rhoifolin and hyperin in mice which infected influenza virus FM1: the normal control group, influenza virus FM1 virus control group and 0.125 g/L, 0.25 g/L, 0.5 g/L and 1.0 g/L dose group of the composition are lavaged respectively with the capacity of 0.4 ml/mouse. Use 10 times of the LD50 FM1 influenza virus to intranasally infect the mice of 20 μl mouse in the groups other than the normal control group 3 d after under mild anesthesia by diethyl ether. Meanwhile, give the same volume of saline solution for the mice in the normal control group. Continue drug administration for 4 groups with administration and give the some dose as above of the saline solution for the mice in the normal control group and influenza virus FM1 virus control group for 8 d. Observe the animal morbidity for 14 days, record the number of deaths and calculate the death rate (death rate=number of deaths in each group/total number of mice in each group×100%). The results are shown in Table 5. (3) Impact of the composition comprising ligustroflavone, rhoifolin and hyperin on lung index of infected influenza virus FM1 in mice: the normal control group, influenza virus FM1 virus control group and 0.125 g/L, 0.25 g/L, 0.5 g/L and 1.0 g/L dose group of the composition comprising ligustroflavone, rhoifolin and hyperin are lavaged respectively with the lavage capacity of 0.4 ml/mouse. Use 1.0 LD50 influenza virus FM1 to intranasally infect the mice of 20 μl/mouse in the groups other than the normal control group under mild anesthesia by diethyl ether 3 d after. Meanwhile, give the same volume of saline solution for the mice in the normal control group. Continue drug administration for 4 groups with administration and give the some dose as above of the saline solution for the mice in the normal control group and influenza virus FM1 virus control group for 8 d. Put the mice to death in the eighth day after virus infection and weigh, take out the lung and weigh and then calculate the lung index (lung index=lung mass/body mass×100%); in addition, take out the spleen and weigh and then calculate the spleen index (spleen index=spleen mass/body mass×100%). The results are shown in Table 6.

TABLE 5

Death Protection Results of the Composition Comprising Ligustroflavone, Rhoifolin and Hyperin on the Infected Influenza Virus FM1 in Mice

| Group | Number of animals | Challenge viral dosage (LD50) | Observation days (day) | Number of deaths | Death rate (%) | Average death days (day) |
|---|---|---|---|---|---|---|
| Normal control group | 10 | — | 14 | 0 | 0 | — |
| Influenza virus model group | 10 | 10 | 14 | 9 | 90 | 4.9 |
| Composition comprising ligustroflavone, rhoifolin and hyperin 1.0 g/L group | 10 | 10 | 14 | 0 | 0** | — |
| 0.5 g/L group | 10 | 10 | 14 | 2 | 20** | 7.4 |
| 0.25 g/L group | 10 | 10 | 14 | 7 | 70* | 6.6 |
| 0.125 g/L group | 10 | 10 | 14 | 9 | 90 | 5.7 |

Note:

**P < 0.01 VS influenza virus model group

*P < 0.05 VS influenza virus model group

TABLE 6

Impact of the Composition Comprising Ligustroflavone, Rhoifolin and Hyperin on Spleen Index and Lung Index of Infected Influenza Virus FM1 in Mice

| Group | Number of animals | Challenge viral dosage (LD50) | Observation days (day) | Spleen index | Lung index | Inhibition rate of lung index (%) |
|---|---|---|---|---|---|---|
| Normal control group | 10 | — | 8 | 0.35 ± 0.04 | 0.97 ± 0.105 | 17.8 |
| Influenza virus model group | 10 | 1 | 8 | $0.45 \pm 0.13^{\#}$ | $1.18 \pm 0.103^{\#}$ | — |

TABLE 6-continued Impact of the Composition Comprising Ligustroflavone, Rhoifolin and
Hyperin on Spleen Index and Lung Index of Infected Influenza Virus FM1 in Mice

| Group | Number of animals | Challenge viral dosage (LD50) | Observation days (day) | Spleen index | Lung index | Inhibition rate of lung index (%) |
|---|---|---|---|---|---|---|
| Composition comprising ligustroflavone, rhoifolin and hyperin 1.0 g/L group | 10 | 1 | 8 | 0.34 ± 0.08* | 0.97 ± 0.153* | 17.8** |
| 0.5 g/L group | 10 | 1 | 8 | 0.35 ± 0.06* | 1.07 ± 0.064* | 9.3* |
| 0.25 g/L group | 10 | 1 | 8 | 0.36 ± 0.03* | 1.11 ± 0.091 | 5.9 |
| 0.125 g/L group | 10 | 1 | 8 | 0.36 ± 0.17* | 1.14 ± 0.332# | 3.4 |

Note:
$P < 0.05$ VS normal control group
Note:
**$P < 0.001$ VS influenza virus model group
*$P < 0.05$ VS influenza virus model group (1) It can be seen from Table 5 that the composition comprising ligustroflavone, rhoifolin and hyperin with the concentration of 0.25~1.0 g/L has a significant inhibitory action on the influenza virus infected mice ($p<0.01$).

(2) It can be seen from Table 6 that the composition with the concentration of 0.5~1.0 g/L has a significant action on the inhibition ratio of the lung index of the influenza virus infected mice ($p<0.01$).

Experimental Data 5: Impact of the Composition Comprising Ligustroflavone, Rhoifolin and Hyperin on Renal Function Impairment.

1) SD rats, 200~240g, Shanghai Sippr-BK Experimental Animal Co., Ltd, Animal Certification No.: SCXK (H) 2003-0002;

2) Reagents and drug: adenine, adenine, (content>98%, imported packing, Shanghai China, Batch No. 20010520), the composition comprising ligustroflavone, rhoifolin and hyperin obtained according to the preparation method in embodiment 3;

3) Test method: feed the male SD rats with the weight of about 220 g with normal diet for 10 d and after normal growth, randomly divide them into the normal control group, administration experimental group and modeling control group according to the weights with each group of 13~15 rats. Creat chronic renal failure (CRF) model with the adenine lavage for the administration experimental group and modeling control group, lavage with 320 mg/(kg·d) adenine and make the suspension of about 2 ml/rat with the distilled water, for 20 d. After 20 days, lavage the rats in the administration experimental group with 2.5 g/(kg·d) of the composition comprising ligustroflavone, rhoifolin and hyperin. Prepare the composition suspension solution (0.625 g/ml) with the distilled water. Lavage the rats by times with about 2 ml/rat each time, lavage the rats in the normal control group and modeling control group with the equal volume of water, anesthetize the rats with diethyl ether 35 d after the administration, take blood from the rat tail artery and observe the indicators.

4) Results:

TABLE 7

Impact of the Composition Comprising Ligustroflavone,
Rhoifolin and Hyperin on Renal Function of CRF rats

| Group | Number of animals | BUN (mmol/L) | SCr (nmol/L) | Hb (g/L) | Ret (%) |
|---|---|---|---|---|---|
| Normal control group | 15 | 7.45 ± 1.21 | 23.88 ± 3.60 | 112.47 ± 6.06 | 13.06 ± 3.04 |
| Modeling control group | 13 | 32.16 ± 3.43 | 84.16 ± 0.93* | 99.58 ± 8.09 | 20.58 ± 6.19 |
| Administration experimental group | 14 | 8.90 ± 2.15** | 25.73 ± 3.43** | 110.88 ± 3.84** | 13.91 ± 3.07** |

Note:
By T test, the result of the experimental group compared with the modeling control group and normal control group. "*" means $P < 0.05$ and "**" means $P < 0.01$.

After the rat CRF modelling by adenine lavage, the rats in the group are listless, with significant weight loss, significantly increased serum Bum and Ser, significantly increased Hb and significantly increased Ret which indicate that the renal functions of the rats are damaged. After treated with the composition comprising ligustroflavone, rhoifolin and hyperin, the rats have no significant differences compared with those in the normal control group and have significant differences compared with those in the modeling group.

Therefore, it can be seen that the composition comprising ligustroflavone, rhoifolin and hyperin has no toxic action on the kidney.

What is claimed is:

1. An extraction method of a composition comprising ligustroflavone, rhoifolin and hyperin from a turpinia montana leaf comprising steps:
   taking the turpinia montana leaf;
   adding 30%~90% ethanol which is 5 to 15 times the amount of the leaf;
   conducting reflux extraction for 1~3 times, with 1~3 hours each time, and then filtering to get filtrate;
   mixing the filtrates gotten from each time of the reflux extraction and recovering the ethanol to get water solution;
   eluting the water solution through a macroporous resin column, collecting elution part,
   reducing pressure, concentrating and drying the elution part, get mixed total glycosides;
   separating the mixed total glycosides by column chromatography to get liquid ligustroflavone, liquid rhoifolin and liquid hyperin respectively,
   crystallizing get the pure ligustroflavone, the pure rhoifolin and the pure hyperin.

2. The method according to claim 1, wherein take the turpinia montana leaf, add 12 times the amount of 70% ethanol, conduct reflux extraction for 1.5 hours and filter to get filtrate, then add 10 times the amount of 70% ethanol in the filter residue, conduct reflux extraction for 1.5 hours and filter to get filtrate, mix the filtrates of the two times, recover the ethanol, elute the water solution through macroporous resin column, collect elution part, reduce pressure, concentrate and dry.

3. The method according to claim 1, wherein the water solution passes through a treated D101 macroporous resin column, elute the water solution with water, 5%~10% ethanol, 30%~55% ethanol and 1% sodium hydroxide solution respectively, collect the 30%~55% ethanol elution part, reduce pressure, concentrate and dry.

4. The method according to claim 1, wherein the mixed total glycosides are subject to a silica gel column chromatography and a Sephadex LH-20 column chromatography isolation, to get liquid ligustroflavone, liquid rhoifolin and liquid hyperin respectively, crystallize respectively, and get the pure ligustroflavone, rhoifolin and hyperin.

5. The method according to claim 2, wherein the water solution passes through a treated D101 macroporous resin column, elute the water solution with water, 5%~10% ethanol, 30%~55% ethanol and 1% sodium hydroxide solution respectively, collect the 30%~55% ethanol elution part, reduce pressure, concentrate and dry.

6. The method according to claim 2, wherein the mixed total glycosides are subject to a silica gel column chromatography and a Sephadex LH-20 column chromatography isolation, to get liquid ligustroflavone, liquid rhoifolin and liquid hyperin respectively, crystallize and get the pure ligustroflavone, rhoifolin and hyperin.

7. The method according to claim 1, wherein the ligustroflavone has a molecular formula of $C_{33}H_{40}O_{18}$, a molecular weight of 724.2 and a structural formula as follows:

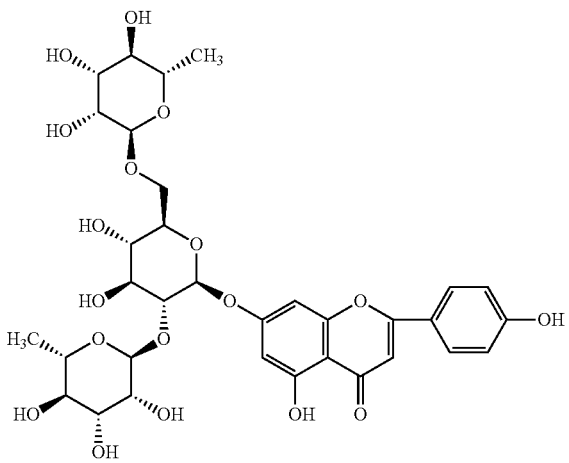 [SMILES: C[C@@H]1O[C@@H](OC[C@H]2O[C@@H](Oc3cc(O)c4c(=O)cc(-c5ccc(O)cc5)oc4c3)[C@H](O[C@@H]3O[C@@H](C)[C@H](O)[C@@H](O)[C@H]3O)[C@@H](O)[C@@H]2O)[C@H](O)[C@H](O)[C@H]1O]

the rhoifolin has a molecular formula of $C_{27}H_{30}O_{14}$, a molecular weight of 578.52 and a structural formula as follows:

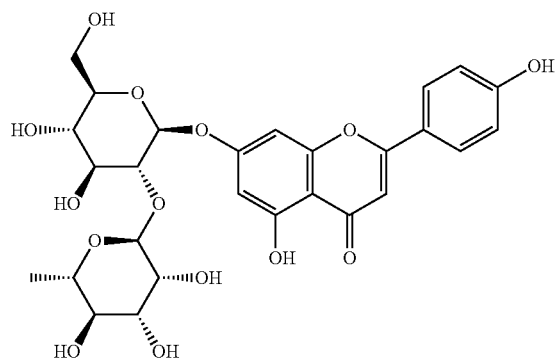 [SMILES: C[C@@H]1O[C@@H](O[C@H]2[C@H](Oc3cc(O)c4c(=O)cc(-c5ccc(O)cc5)oc4c3)O[C@H](CO)[C@@H](O)[C@@H]2O)[C@H](O)[C@H](O)[C@H]1O]

the hyperin has a molecular formula of $C_{21}H_{20}O_{12}$, a molecular weight of 464.38 and a structural formula as follows:

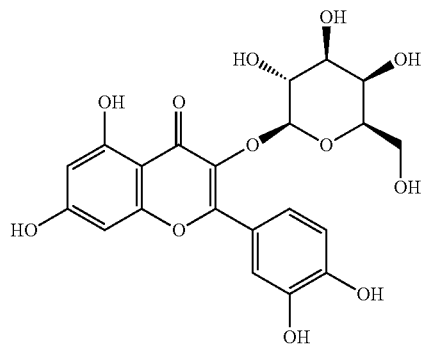 [SMILES: O=c1c(O[C@@H]2O[C@H](CO)[C@H](O)[C@H](O)[C@H]2O)c(-c2ccc(O)c(O)c2)oc2cc(O)cc(O)c12]

a rational weight ratio of the composition is 40% to 80% ligustroflavone, 5% to 45% rhoifolin and 1% to 40% hyperin.

* * * * *